US008710073B2

(12) United States Patent
Bernadou et al.

(10) Patent No.: US 8,710,073 B2
(45) Date of Patent: Apr. 29, 2014

(54) ANTI-INFECTIVE DERIVATIVES, METHOD FOR THE PRODUCTION THEREOF, PHARMACEUTICAL COMPOSITIONS CONTAINING SAME AND USES OF SAID DERIVATIVES IN TREATMENT

(75) Inventors: Jean Bernadou, Toulouse (FR); Vania Bernardes-Genisson, Toulouse (FR); Tamara Delaine, Toulouse (FR); Annaïck Quemard, Montgiscard (FR)

(73) Assignees: Centre National de la Recherche Scientifique (C.N.R.S.), Paris (FR); Universite Paul Sabatier Toulouse III, Toulouse Cedex (FR)

( * ) Notice: Subject to any disclaimer, the term of this patent is extended or adjusted under 35 U.S.C. 154(b) by 234 days.

(21) Appl. No.: 12/866,645

(22) PCT Filed: Feb. 6, 2009

(86) PCT No.: PCT/FR2009/050195
§ 371 (c)(1),
(2), (4) Date: Nov. 30, 2010

(87) PCT Pub. No.: WO2009/101345
PCT Pub. Date: Aug. 20, 2009

(65) Prior Publication Data
US 2011/0092536 A1 Apr. 21, 2011

(30) Foreign Application Priority Data
Feb. 7, 2008 (FR) ...................................... 08 50778

(51) Int. Cl.
*A61K 31/438* (2006.01)
*C07D 471/04* (2006.01)
*C07D 211/90* (2006.01)
*A61K 31/455* (2006.01)
*A61P 31/06* (2006.01)
*A61P 31/08* (2006.01)
*A61P 31/00* (2006.01)
*A61P 31/04* (2006.01)
*A61P 33/06* (2006.01)

(52) U.S. Cl.
USPC ............ 514/300; 514/355; 546/113; 546/316

(58) Field of Classification Search
USPC ............................ 546/113, 316; 514/300, 355
See application file for complete search history.

(56) References Cited

U.S. PATENT DOCUMENTS 6,328,793 B1 12/2001 Malhotra et al.
7,241,805 B2 * 7/2007 Oberegger et al. ............ 514/463

FOREIGN PATENT DOCUMENTS

JP 2003521550 A 7/2003
WO 99/23151 A1 5/1999
WO 2008/009122 A1 1/2008

OTHER PUBLICATIONS

Broussy et al., J. Org. Chem.(2005), vol. 70, pp. 10502-10510.*
Bahajaj et al., Journal of the Chemical Society, Perkin Transactions 1: Organic and Bio-Organic Chemistry (1996), (10), 1041-1046.*
El-Sharief et al., Egyptian Journal of Chemistry (1982), Volume Date 1981, 24(4-6), 435-43.*
Vollmann et al., Chemische Berichte (1972), 105(9), 2933-54.*
Topliss et al., Journal of Medicinal Chemistry (1964), 7(4), 453-6.*
Sylvain Broussy, et al. "The First Chemical Synthesis of the Core Structure of the Benzoylhydrazine-NAD Adduct, a Competitive Inhibitor of the Mycobacterium tuberculosis Enoyl Reductase", J.Org.Chem, 2005, pp. 10502-10510, vol. 70, XP-002496833.
Masaru Ogata, et al. "Synthesis and antimycotic properties of 3-(1-imidazolyl) indolin-2-ones" European Journal of Medicinal chemistry—Chimica Therapeutica, Jul.-Aug. 1981, pp. 373-379, vol. 16, No. 4, XP-009078474.
Rudolph A. Abramovitch, et al. "New Ring Systems from 1,2-Benzisothiazole-1, 1-Dioxides and Related Compounds", Tetrahedron, 1996, pp. 3339-3354, vol. 52, No. 9, XP-4104357.
CrossFire Beilstein Database, Beilstein Institute for Organic Chemistry, Frankfurt-Main, DE, 1985, Database accession No. BRN:5543587, pp. 167-182, vol. 1, XP-002496835.
Crossfire Beilstein Database, Beilstein Institute for Organic Chemistry, Frankfurt-Main, DE, 1972, Databese accession No. BRN: 1623583, pp. 2128-2131, vol. 20, XP-002496836.
CrossFire Beilstein Database, Beilstein Institute for Organic Chemistry, Frankfurt-Main, DE, 1972, Databese accession No. BRN:1586486, pp. 2933-2954, vol. 105, XP-002496837.
CrossFire Beilstein Database, Beilstein Institute for Organic Chemistry, Frankfurt-Main, DE, 1996, Database accession No. BRN: 1536983, pp. 1041-1046, vol. 10, XP-002496838.
CrossFire Beilstein Database, Beilstein Institute for Organic Chemistry, Frankfurt-Main, DE, 1996, Database accession No. BRN: 1538404, pp. 1600-1606, XP-002496839.
Database Caplus, Chemical Abstracts Service, Columbus, Ohio, Extrait de STN accession No. 1983:521944, Database accession No. 99:121944, 1982, pp. 4-6, vol. 24, X-P002496840.
Database Caplus, Chemical Abstracts Service, Columbus, Ohio, Extrait de STN accession No. 1987:50081, Database accession No. 106:50081, 1986, pp. 19-27, vol. 24, X-P002496841.
Marcel K. Eberle, et al. "The preparation of 11-Aryl-11H-isoindolo[2,1-a]benzimidazol-11-ols", J. Org. Chem., 1973, pp. 3872-3874, vol. 38, No. 22, XP-002496834.
Mukaiyama et al., "A Novel Carbocationic Species paired with Tetrakis(pentafluorophenyl)borate Anion in Catalytic Aldol Reaction", Chemistry Letters, 2000, p. 606-607.

* cited by examiner

*Primary Examiner* — Niloofar Rahmani
(74) *Attorney, Agent, or Firm* — Sughrue Mion, PLLC; Richard Turner

(57) ABSTRACT

The present invention relates to bi-substrate inhibitor molecules combining (i) a pyridine, pyridinium or dihydropyridine-type structure allied to active metabolites of isoniazide, or related structures, and (ii) a hydrophobic substituent. The invention also relates to the method for preparing said molecules, to the pharmaceutical compositions containing said molecules, and to the use thereof as inhibitors of enoyl reductase for the preparation of a drug, especially an anti-infective drug for the treatment of tuberculosis.

15 Claims, No Drawings

ANTI-INFECTIVE DERIVATIVES, METHOD FOR THE PRODUCTION THEREOF, PHARMACEUTICAL COMPOSITIONS CONTAINING SAME AND USES OF SAID DERIVATIVES IN TREATMENT

The present invention relates to bi-substrate inhibitor molecules combining a hydrophobic substituent with an analogue of the active metabolite of isoniazide, to the method for the preparation thereof, to pharmaceutical compositions containing them, and to the use thereof, in particular as enoyl-ACP (acyl carrier protein) reductase inhibitors, for the preparation of an anti-infective drug, in particular an antituberculous drug.

In the fight against infectious diseases, the medical profession is constantly seeking new active molecules for effectively combating the crucial problem of resistance. In this respect and by way of example, the treatment of tuberculosis, a disease which has undergone a very disconcerting worldwide revival over the last twenty years or so, poses the problem of replacing the current front-line antibiotics, the efficacy of which has been greatly affected by the resistance developed by the germ responsible for this illness.

The invention is based on rationally designing new compounds on the basis of an improved knowledge of the mechanism of action of a reference drug and of resistance mechanisms.

The fatty acid elongation system (fatty acid synthase II or FAS-II system) is necessary for the biosynthesis of mycolic acids, specific constituents and essential components of the envelope of mycobacteria, in particular *Mycobacterium tuberculosis* (or Koch's *bacillus*), the pathogen for tuberculosis, *M. leprae*, the pathogen for leprosy, and other mycobacteria which are opportunistic pathogens (for example *M. avium, M. ulcerans, M. marinum*). This potential therapeutic target is also found in some other infectious agents (for example *Plasmodium falciparum*, the parasite responsible for malaria).

Isoniazide (INH) is a front-line antituberculous antibiotic, the efficacy of which is increasingly being limited by the appearance of new, resistant strains of *M. tuberculosis*. It is a pro-drug which is activated by oxidation in the mycobacterium due to a catalase peroxidase (KatG), forming covalent isonicotinoyl-NAD (INH-NAD) adducts considered to be the active metabolites of isoniazide. These adducts are excellent inhibitors of InhA, an enzyme in the FAS-II system. Analogous adducts, isonicotinoyl-NADP (INH-NADP), also inhibit another enzyme in the FAS-II system, the protein MabA, which has a 3D structure related to that of InhA. The resistance phenomena which occur are largely due to mutations which principally affect the KatG enzyme (lack of activation). Mutations are also similarly encountered, in a smaller proportion, in the target enzyme InhA (loss of affinity of the inhibitor adduct for its target in vivo) or its promoter (overproduction of the target). Designing bi-substrate inhibitors which do not require a prior activation step by way of KatG, and which ideally interact within the InhA active site with regions of the protein which exclude the most frequently encountered mutation sites, should make it possible largely to overcome the current problems of INH resistance.

The present inventors have therefore developed bi-substrate InhA inhibitors combining (i) a unit derived from the active metabolites of isoniazide of the pyridine, pyridinium or dihydropyridine type and related structures, and (ii) a hydrophobic substituent targeting the site of the substrate.

Whilst not limited by theory, the compounds identified by the present invention also have other targets and exhibit inhibitory properties towards bacterial strains without an InhA equivalent, making them anti-infective compounds having a wide range of applications.

The present invention relates to compounds of general formula (I):

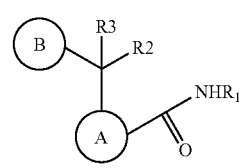

(I)

in the form of a base or an acid addition salt, as well as in the form of a pharmaceutically acceptable hydrate or solvate, in which:

the cycle

represents a 6-membered aromatic or non-aromatic ring, optionally comprising one or more nitrogen atoms, said nitrogen atom(s) optionally being substituted by an optionally substituted tetrahydrofuran group, such as 2-hydroxymethyl-tetrahydrofuran-3,4-diol; or by a —CH$_2$-E group, wherein E represents an electron-attracting group such as —CONRR'; —CO—SR; phenyl substituted for example by a CN or NO$_2$ group; —CO—Oalkyl; —CO—Oalkyl-OH; —O-alkyl-OAc; wherein R and R' are the same or different and independently represent a hydrogen atom or an alkyl group;

more preferably, the nitrogen atom is optionally substituted by a group selected from the groups —CH$_2$—CO—Oalkyl; —CH$_2$—CO—Oalkyl-OH; —CH$_2$—O-alkyl-OAc;

and/or wherein said nitrogen atom(s) may be in the form of pyridinium salts, the counter ion being the anion of a halogen atom, such as bromide or another pharmaceutically acceptable anion.

Preferably,

is an optionally substituted phenyl, pyridine, pyrazine or dihydropyridine ring.

More preferably,

represents a dihydropyridine or pyridine group, optionally substituted by a group selected from the groups —CH$_2$—CO—Oalkyl, —CH$_2$—CO—Oalkyl-OH, —CH$_2$—O-alkyl-OAC, and/or optionally in the form of a pyridinium halide;

(B)

represents a 5-to-10-membered mono- or bicyclic aryl or heteroaryl group, substituted by one or more groups selected from the groups —OH; —($C_5$-$C_{20}$)alkyl; —O($C_2$-$C_{20}$)alkyl; —S(O)$_p$alkyl wherein p=0, 1 or 2; alkenyl; alkynyl; —Oalkenyl; —C(=)O-alkyl; —C(=O)-alkenyl; phenyl substituted by an alkyl group; cycloalkyl optionally substituted by an alkyl group.

Preferably, (B)

is a phenyl ring substituted by one or more groups selected from the groups —OH; —($C_5$-$C_{20}$)alkyl; —O($C_5$-$C_{20}$)alkyl; —S(O)$_p$($C_5$-$C_{20}$)alkyl wherein p=0, 1 or 2; ($C_5$-$C_{20}$)alkenyl; ($C_5$-$C_{20}$)alkynyl; —O($C_5$-$C_{20}$)alkenyl; —C(=)O—($C_5$-$C_{20}$)alkyl; —C(=O)—($C_5$-$C_{20}$)alkenyl; phenyl substituted by a ($C_5$-$C_{20}$) alkyl group; and cycloalkyl optionally substituted by an alkyl group.

More preferably, (B)

is a phenyl ring substituted by a —OH, ($C_5$-$C_{20}$)alkyl, O($C_5$-$C_{20}$)alkenyl, O($C_5$-$C_{20}$)alkyl or —S(O)$_p$alkyl group wherein p=0, 1 or 2.

More preferably, (B)

is substituted in the ortho or meta position;

R1 represents a hydrogen atom or an alkyl group and R2 and R3 together form an =O group;

or alternatively

R3 represents an —OH or —Oalkyl group and R2 forms, together with R1, a single bond binding the nitrogen atom to the carbon atom substituted by R3, (A) and (B), in such a way as to form an indanone ring by fusion with the cycle (A).

Preferably, R3=OH or —Oalkyl and R1 and R2 together form a single bond, or R3 and R2 form an =O group and R1 represents a hydrogen atom.

In the above and in the following, the groups —C(=O)NHR1 and C(R3)(R2)- are understood to be located in two adjacent positions on the ring (A).

The compounds of formula (I) may comprise one or more asymmetric carbon atoms. They may therefore exist in the form of enantiomers or diastereoisomers. These enantiomers and diastereoisomers and the mixtures thereof, including racemic mixtures, are part of the invention.

The compounds of formula (I) may exist in the form of bases or acid addition salts. Addition salts of this type are part of the invention.

These salts can be prepared with pharmaceutically acceptable acids, but the salts of other acids which can be used, for example, for the purification or isolation of the compounds of formula (I) are also part of the invention.

The compounds of formula (I) may also exist in the form of hydrates or solvates, namely in the form of associations or combinations with one or more water molecules or with a solvent. Hydrates and solvates of this type are also part of the invention.

In the context of the present invention:

halogen atom means a fluorine, chorine, bromine or iodine;

alkyl group means a linear or branched saturated aliphatic group having 1 to 20 carbon atoms, unless stated otherwise. Examples include methyl, ethyl, propyl, isopropyl, butyl, isobutyl and tert-butyl groups;

cycloalkyl group means a cyclic alkyl group having 3 to 10 carbon atoms. Examples include cyclopropyl, methylcyclopropyl, cyclobutyl, cyclopentyl, cyclohexyl etc.;

alkenyl group means a linear or branched, mono- or polyunsaturated aliphatic group of 2 to 20 carbon atoms, comprising for example one or two ethylenic unsaturations;

alkynyl group means a linear or branched, mono- or polyunsaturated aliphatic group of 2 to 20 carbon atoms, comprising for example one or two acetylenic unsaturations;

aryl group means a cyclic aromatic group comprising between 5 and 10 carbon atoms. Examples of aryl groups include phenyl and naphthyl;

heteroaryl group means a cyclic aromatic group comprising between 5 and 10 carbon atoms and comprising between 1 and 3 heteroatoms, such as nitrogen, oxygen or sulphur. Examples of heteroaryl groups include pyridine in particular.

Compounds of formula (I) are particularly preferred in which:

(A)

represents a dihydropyridine group, optionally substituted by a group selected from —CH$_2$COOalkyl, —CH$_2$COOalkylOH;

Ⓑ represents a phenyl group, substituted in the ortho or meta position, preferably the meta position, by a group selected from the groups $C_5$-$C_{20}$ alkyl, —Oalkyl, —Oalkenyl, —OH, phenyl optionally substituted by alkyl;

R1 and R2 together form a single bond and R3=OH, or R1=H and R2 and R3 together form an =O group;

in the form of a base or an acid addition salt, as well as in the form of a pharmaceutically acceptable hydrate or solvate.

Compounds of formula (I) according to the invention include in particular the following compounds:

1-(3-dodecylphenyl)-1-hydroxy-1,2-dihydropyrrolo[3,4-c]pyridin-3-one;

1-(3-dodecyloxyphenyl)-1-hydroxy-1,2-dihydropyrrolo[3,4-c]pyridin-3-one;

1-(3-dodecylphenyl)-5-[2-(ethyloxy)-2-oxoethyl]-1-hydroxy-3-oxo-1,2-dihydropyrrolo[3,4-c]pyridinium bromide;

ethy 3-aminocarbonyl-[4-(3-dodecylbenzoyl)-1,4-dihydro-pyridin-1-yl]acetate;

1-(3-octyloxyphenyl)-1-hydroxy-1,2-dihydro-3H-pyrrolo[3,4-c]pyridin-3-one;

1-(2-dodecyloxyphenyl)-1-hydroxy-1,2-dihydro-3H-pyrrolo[3,4-c]pyridin-3-one;

1-(3-octodecyloxyphenyl)-1-hydroxy-1,2-dihydro-3H-pyrrolo[3,4-c]pyridin-3-one;

1-[3-(dodecylthio)phenyl]-1-hydroxy-1,2-dihydro-3H-pyrrolo[3,4-c]pyridin-3-one;

1-(3-dodecyloxyphenyl)-1-methoxy-1,2-dihydro-3H-pyrrolo[3,4-c]pyridin-3-one;

1-hydroxy-1-(3-(propen-3-yl)oxyphenyl)-1,2-dihydropyrrolo[3,4-c]pyridin-3-one;

1-hydroxy-1-(3-hydroxyphenyl)-1,2-dihydropyrrolo[3,4-c]pyridin-3-one;

1-hydroxy-1-(3-octylphenyl)-1,2-dihydropyrrolo[3,4-c]pyridin-3-one;

1-hydroxy-1-(3-(4-nonylphenyl)phenyl)-1,2-dihydropyrrolo[3,4-c]pyridin-3-one;

1-[3-(dodecyloxy)phenyl]-5-(2-ethoxy-2-oxoethyl)-1-hydroxy-3-oxo-2,3-dihydro-1H-pyrrolo[3,4-c]pyridin-5-ium bromide;

1-[(3-(dodecyloxy)phenyl)-1-hydroxy-5-[2-(3-hydroxypropoxy)-2-oxyethyl]-3-oxo-2,3-dihydro-1H-pyrrolo[3,4-c]pyridin-5-ium bromide;

ethyl 3-aminocarbonyl-[4-(3-dodecyloxybenzoyl)-1,4-dihydropyridin-1-yl]acetate;

3-hydroxypropyl 3-aminocarbonyl-[4-(3-dodecyloxybenzoyl)-1,4-dihydropyridin-1-yl]acetate;

in the form of a base or an acid addition salt, as well as in the form of a pharmaceutically acceptable hydrate or solvate.

The present application further relates to the method for the preparation of compounds of general formula (I).

According to the invention, the compounds of general formula (I) can be prepared by the following method.

More precisely, in a first embodiment, the compounds of general formula (I) in which R1 and R2 together form a single bond and R3 represents —OH can be prepared by coupling a compound of general formula (II):

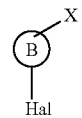

(II)

and a compound of general formula (III):

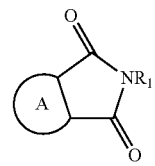

(III)

resulting in a compound of formula (IV):

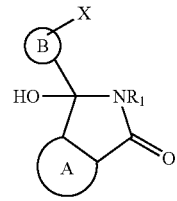

(IV)

in which

Ⓐ, Ⓑ and R1 are defined as in general formula (I), Hal represents a halogen atom and X represents a hydrogen atom, when

Ⓑ is not substituted, or the substituent of

Ⓑ corresponding to the desired general formula (I) (in these two cases, the compound (IV) corresponds to the compound (I)), or a halogen atom, the coupling being followed in this case by the reaction substituting the halogen atom of the compound (IV) with the appropriate substituent of

Ⓑ corresponding to the desired general formula (I).

The coupling reaction generally takes place in the presence of an organic or inorganic base such as n-BuLi or t-BuLi, in a solvent such as THF, at a temperature between −78° and ambient temperature, in an inert atmosphere.

The substitution reaction is generally carried out by applying or adapting substitution reactions known to the person skilled in the art, using appropriate reagents. These substitution reactions are described for example in March's *Advanced Organic Chemistry*, 5th Ed., John Wiley and Sons, Inc. or Larock, *Comprehensive Organic Transformations*, VCH Ed. A representative example is the substitution reaction resulting in the compound of general formula (I) in which (B)

is substituted by an alkyl group. This reaction may in particular be carried out using alkylboronic acid in the presence of diphenylphosphino ferrocene palladium (II) chloride, silver oxide and potassium carbonate.

The compound of general formula (II) is commercially available or may be prepared by applying or adapting known methods for substituting the ring (B)

as desired to obtain the compound of formula (I) in which (B)

is substituted. For example, the ring (B)

may be substituted by an Oalkyl group using a corresponding starting material (II) in which (B)

is substituted by a hydroxy group, by reacting a compound of the alkyl halide type in the presence of a base such as potassium carbonate.

According to a second embodiment, the compounds of general formula (I) in which R1 and R2 together form a single bond and R3 represents —OH may be prepared by cyclising compounds of general formula (V):

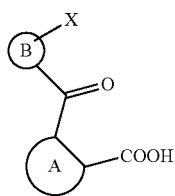

(V)

in which (A), (B)

and Hal are defined as in general formula (IV) in the presence of NHR1 (V'), resulting in the compound of formula (IV):

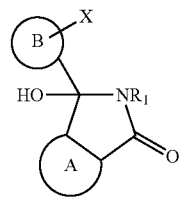

(IV)

in which R1 is defined as in general formula (I) and X represents a hydrogen atom, when (B)

is not substituted, or the substituent of (B)

corresponding to the desired general formula (I) (in these two cases, the compound (IV) corresponds to the compound (I)), or a halogen atom, the cyclisation being followed in this case by the reaction substituting the halogen atom of the compound (IV) with the appropriate substituent of (B)

corresponding to the desired general formula (I).

The cyclisation reaction is generally carried out using thionyl chloride to form the corresponding acyl chloride, followed by the addition of a compound (V') of formula

NHR1          (V')

This reaction is generally carried out without intermediate isolation of the acyl chloride, at a temperature between ambient temperature and the boiling point of the reaction mixture.

The compound of formula (V') may in particular be ammonium hydroxide dissolved in water.

The substitution reaction is generally carried out as discussed above.

The compound of formula (V) may be obtained from a compound of formula (VI):

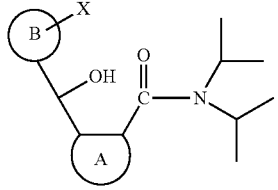
(VI)

in which

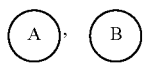

and X are defined as in general formula (V). This reaction is generally carried out in an acidic medium, for example in formic acid, at a temperature between ambient temperature and the reflux temperature of the reaction mixture.

The compound of formula (VI) may be obtained by reduction of the corresponding compound of formula (VII):

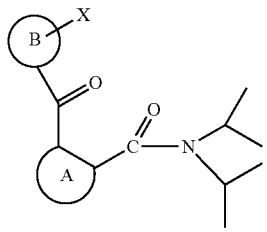
(VII)

in which

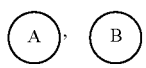

and X are defined as in general formula (VI). This reaction can generally be carried out using a reducing agent such as sodium tetraborohydride, in a solvent such as an alcohol, for example ethanol.

The compound of formula (VII) can be prepared by coupling corresponding compounds of formulae (VIII) and (IX):

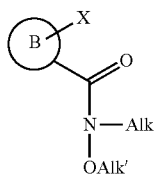
(VIII)

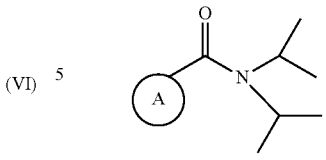
(IX)

in which

and X are as defined in general formula (VII) and Alk and Alk' are the same or different and independently represent an alkyl group. This reaction is generally carried out in the presence of a base such as a lithium-based compound, for example lithium diisopropylamide, in an appropriate organic solvent, such as diethyl ether. This reaction is preferably carried out in an anhydrous medium, in an inert atmosphere, by adding the base to the compound of formula (IX) and then adding the compound of general formula (VIII). This reaction is preferably carried out at a temperature between −75° C. and 0° C.

The compound of formula (VIII) may be obtained by coupling corresponding compounds of formulae (X) and (XI):

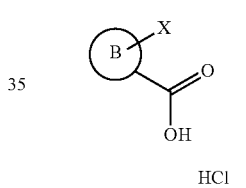
(X)

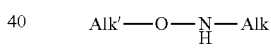
(XI)

in which

X, Alk and Alk' are defined as in general formula (VIII). This reaction is generally carried out using coupling reagents of the EDCI type, such as 1-(3-dimethylaminopropyl)-3-ethyl-carbodiimide (hydrochloride salt), and of the HOBT type (1-hydroxy-1H-benzotriazole hydrate) and in the presence of a base such as triethylamine.

When

represents a pyridinium ring in which the nitrogen atom is quaternised, the preparation method further comprises the step of quaternising the compound of general formula (I) in which

represents a pyridine ring using a compound of general formula (XII):

R-Hal (XII)

in which Hal represents a halogen atom, such as bromine, and R represents a group of the —CH$_2$E type, E being an electron-attracting group defined as in general formula (I). This reaction is generally carried out in a solvent such as anhydrous tetrahydrofuran, at a temperature between ambient temperature and the reflux temperature of the reaction mixture.

When

represents a dihydropyridine ring and R2 and R3 together form an =O group and R1 represents a hydrogen atom, the compound of general formula (I) can be obtained by reduction from the compound of general formula (I) in which

represents a pyridinium ring. The reducing agent may in particular be sodium triacetoxyborohydrate in an acetic medium. This reaction is generally carried out at a temperature between −10° C. and ambient temperature.

Diagram 1 below illustrates the method according to the invention.

Diagram 1

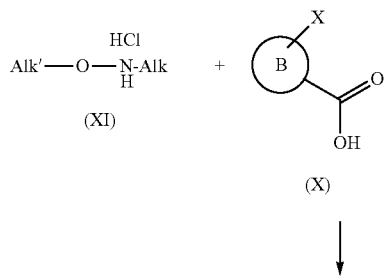

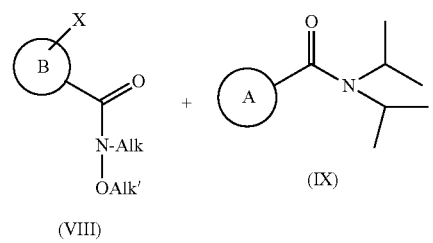

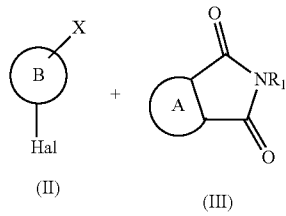

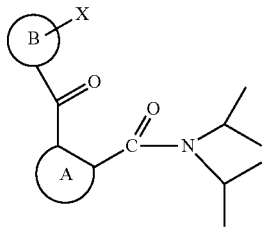

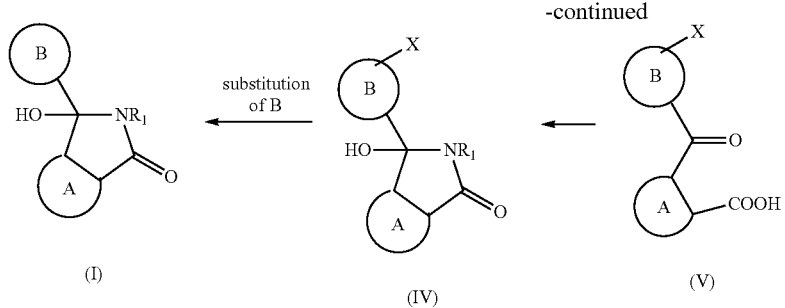

(I)　(IV)　(V)　(VI)

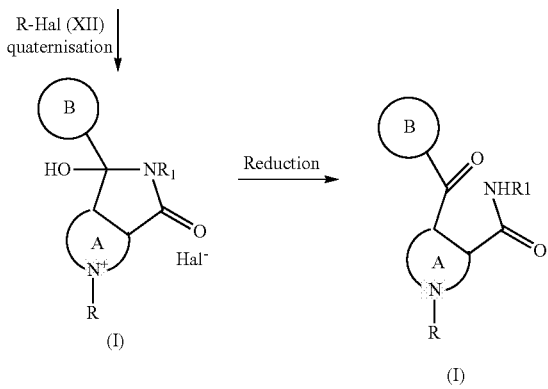

(I)　(I)

The method according to the invention optionally comprises the subsequent step of isolating the desired product obtained.

The starting materials (II), (III), (IX), (X), (XI) and the appropriate reagents are commercially available or may be prepared by applying or adapting methods known to the person skilled in the art.

The compounds according to the invention have noteworthy anti-infective properties.

According to a further aspect therefore the invention relates to drugs comprising a compound of formula (I)

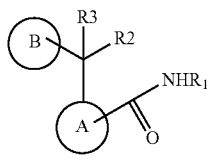

(I)

in which:

the cycle

represents a 6-membered aromatic or non-aromatic ring, optionally comprising one or more nitrogen atoms, said nitrogen atom(s) optionally being substituted by an optionally substituted tetrahydrofuran group, such as 2-hydroxymethyl-tetrahydrofuran-3,4-diol; or by a —CH$_2$-E group, wherein E represents an electron-attracting group such as —CONRR'; —CO—SR; —CO—Oalkyl; —CO—Oalkyl-OH; —O-alkyl-OAc; phenyl substituted for example by a CN or NO$_2$ group; wherein R and R' are the same or different and independently represent a hydrogen atom or an alkyl group;

and/or wherein said nitrogen atom(s) may be in the form of pyridinium salts, the counter ion being the anion of a halogen atom, such as bromide;

represents a 5-to-10-membered mono- or bicyclic aryl or heteroaryl group, substituted by one or more groups selected from the groups —OH; —(C$_5$-C$_{20}$)alkyl; —Oalkyl; —S(O)$_p$alkyl wherein p=0, 1 or 2; alkenyl; alkynyl; —Oalkenyl; —C(=)O-alkyl; —C(=O)-alkenyl; phenyl optionally substituted by an alkyl group; cycloalkyl optionally substituted by an alkyl group;

R1 represents a hydrogen atom or an alkyl group and R2 and R3 together form an =O group;

or alternatively

R3 represents an —OH or —Oalkyl group and R2 forms, together with R1, a single bond binding the nitrogen atom to the carbon atom substituted by R3,

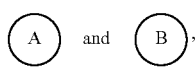

in such a way as to form an indanone ring by fusion with the cycle (A);

the groups —C(=O)NHR1 and C(R3)(R2)- being understood to be located in two adjacent positions on the ring (A);

in the form of a base or an acid addition salt, as well as in the form of a pharmaceutically acceptable hydrate or solvate; and at least one pharmaceutically acceptable excipient.

Thus, the compounds according to the invention can be used as anti-infective agents in humans or animals, in particular in the treatment or prevention of:

mycobacterioses, in particular tuberculosis, leprosy or opportunistic diseases, such as those caused by *Mycobacterium avium, M. bovis, M. marinum* and/or *M. ulcerans*;

malaria;

any infection caused by a pathogen having an enzyme of the enoyl acyl carrier protein reductase type or an enzyme of a related structure, belonging to the short chain dehydrogenase reductase (SDR) superfamily.

More preferentially, the compounds according to the invention may be used in the treatment of tuberculosis.

According to a further aspect the present invention relates to pharmaceutical compositions comprising a compound according to the invention as an active ingredient. These pharmaceutical compositions contain an effective dose of at least one compound according to the invention, or a pharmaceutically acceptable salt, a hydrate or solvate of said compound, as well as at least one pharmaceutically acceptable excipient.

Said excipients are selected from the conventional excipients known to the person skilled in the art in accordance with the desired pharmaceutical form and delivery system.

In the pharmaceutical compositions of the present invention for oral, sublingual, subcutaneous, intramuscular, intravenous, topical, local, intratracheal, intranasal, transdermal or rectal administration, the active ingredient of formula (I) above, or possibly the salt, solvate or hydrate thereof, may be administered to animals and to humans in a unitary administration form, in a mixture with conventional pharmaceutical excipients, for the prophylaxis or treatment of the above disorders or diseases.

The appropriate unitary administration forms comprise oral forms such as tablets, hard or soft capsules, powders, granules and oral solutions or suspensions, sublingual, buccal, intratracheal, intraocular and intranasal administration forms, inhalation, topical, transdermic, subcutaneous and intramuscular or intravenous administration forms, rectal administration forms and implants. For topical application, the compounds according to the invention can be used in creams, gels, ointments or lotions.

The pharmaceutical compositions according to the invention may comprise 10 to 800 mg of a compound of general formula (I) according to the invention as an active ingredient.

For example, a unitary administration form of a compound according to the invention in the form of a tablet may comprise the following ingredients:

| Compound according to the invention | 50.0 mg |
| Mannitol | 224 mg |
| Croscarmellose sodium | 6.0 mg |
| Maize starch | 15.0 mg |
| Hydroxypropyl methylcellulose | 2 mg |
| Magnesium stearate | 3.0 mg |

The dosage of active ingredient administered each day may amount to 0.01 to 100 mg/kg, in one or more doses, preferably 0.02 to 50 mg/kg.

There may be particular cases where higher or lower dosages are appropriate; dosages of this type do not depart from the scope of the invention. In conventional practice, the appropriate dosage for each patient is determined by the doctor in accordance with the delivery system and the weight and the response of said patient.

The present invention also further relates to combinations of a compound of general formula (I) according to the invention and an anti-infective active ingredient. Examples of anti-infective compounds include in particular isoniazide, rifampicine, pyrazinamide, ethambutol, chloroquine, and any other antibiotic molecule in current clinical use.

The following examples disclose the preparation of particular compounds according to the invention. These examples are non-limiting and merely illustrate the present invention. The numbers of the example compounds correspond to those given in the table hereinafter, which illustrates the chemical structures and the physical properties of some compounds according to the invention.

All of the solvents used are of "reagent grade" or "HPLC grade" purity.

The present invention also relates to the method for preparing the aforementioned molecules of general formula (I).

The present invention also further relates to the use of the compounds of general formula (I) in therapeutics.

The following examples are given for illustrative purposes and do not limit the present invention.

PREPARATION 1

Synthesis of Compound 1 of Formula

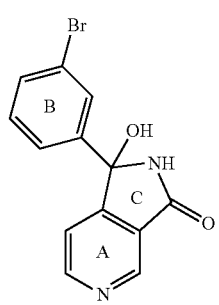

1

Step 1: Synthesis of a Compound (1a)

Compound 1a has the following formula:

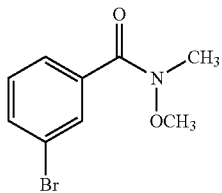

Triethylamine (2.9 ml, 19.3 mmol) is added dropwise, in an inert atmosphere, to a suspension of 3-bromobenzoic acid (4.0 g, 20.0 mmol), N,O-dimethylhydroxylamine hydrochloride (2.0 g, 21.0 mmol), 1-hydroxy-1H-benzotriazole hydrate (920 mg, 6.0 mmol) and 1-(3-dimethylaminopropyl)-3-ethylcarbodiimide (4.6 g, 24.0 mmol) in anhydrous acetonitrile (25 ml). After 2 h of stirring at ambient temperature, 20 ml of distilled water are added to the reaction mixture, and then the solvent is evaporated at a reduced pressure. The residue is taken up by the water and extracted with ethyl acetate (3×20 ml). The organic phases are combined, dried over anhydrous sodium sulphate, and concentrated on a rotating evaporator yielding 4.7 g (98%) of amide 1a in the form of a pale yellow oil.

IR (film, $cm^{-1}$): 3066, 2969, 2934, 1644, 1383, 1211, 662. NMR $^1H$ (250 MHz, $CDCl_3$) δ (ppm): 7.80 (t, 2H), 7.61-7.54 (m, 2H), 7.26 (t, 1H), 3.53 (s, 3H), 3.34 (s, 3H). NMR $^{13}C$ (50 MHz, $CDCl_3$) δ (ppm): 168.0, 135.6, 133.4, 131.0, 129.4, 126.6, 121.8, 61.0, 33.4. HR-MS (FAB) for $C_9H_{11}NO_2Br$: observ. 243.9969, theor. 243.9973.

Step 2: Synthesis of a Compound (1b) Having a Diisopropylnicotinamide Ring Comprising a 3-bromobenzoyl Radical in the 4 Position Compound 1b has the following formula:

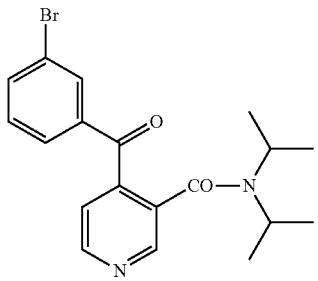

Lithium diisopropylamide (2.7 ml, 5.4 mmol, 2M in solution in THF/n-heptane) is added dropwise, at −78° C., in an inert atmosphere, to a solution of N,N-diisopropylnicotinamide (618 mg, 3.0 mmol) in anhydrous diethyl ether (75 ml). After 20 minutes of stirring at −50° C., a solution of Weinreb amide 1a (1.1 g, 4.5 mmol) in anhydrous diethyl ether (8 ml) is added dropwise at −78° C. 8 times, every 10 minutes. The reaction medium is left to return to ambient temperature while stirring and the reaction is followed by CCM (eluent: dichloromethane/methanol: 95/5). Subsequently, 50 ml of distilled water are added to the solution, and the reaction mixture is extracted with ethyl acetate (4×20 ml). The organic phases are combined, washed with a saturated sodium chloride solution, dried over anhydrous sodium sulphate and concentrated on a rotating evaporator. The oily residue obtained is purified by chromatography in a silica gel column (eluent: dichloromethane/methanol gradient from 100/0 to 98/2), yielding 330 mg (28%) of the ketoamide 1b in the form of a yellow solid.

$P_f$: 112° C. IR (KBr, $cm^{-1}$): 3061, 2971, 2933, 1675, 1630, 1343, 1267, 668. NMR $^1H$ (250 MHz, $CDCl_3$) δ (ppm): 8.71 (d, 1H), 8.63 (s, 1H), 7.94 (t, 1H), 7.73-7.66 (m, 2H), 7.32 (t, 1H), 7.30 (d, 1H), 3.87-3.77 (m, 1H), 3.52-3.41 (m, 1H), 1.38 (d, 6H), 1.22 (d, 6H). NMR $^{13}C$ (63 MHz, $CDCl_3$) δ (ppm): 193.5, 166.4, 149.4, 146.9, 143.6, 137.4, 133.6, 122.8, 136.5, 132.6, 130.1, 128.8, 122.2, 51.7, 42.4, 20.5, 20.0. HR-MS (ESI) for $C_{19}H_{22}N_2O_2Br$: observ. 389.0864; theor. 389.0865.

Step 3: Reduction of the Carbonyl Function of the Amidoketone 1b Obtained in Step 2

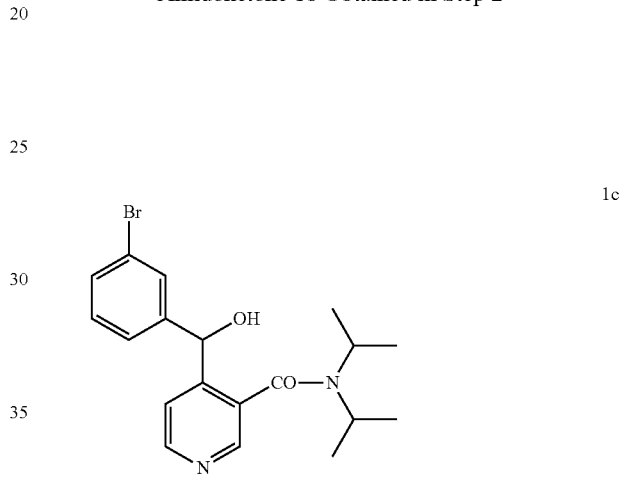

Sodium tetraborohydride (421 mg, 8.8 mmol) is added to a solution of ketoamide 1b (627 mg 1.6 mmol) in absolute ethanol (80 ml). After 3 h of stirring at ambient temperature, 50 ml of distilled water are added. The reaction mixture is extracted with dichloromethane (3×20 ml). The organic phases are combined, dried over anhydrous sodium sulphate and concentrated on a rotating evaporator, yielding 631 mg (85%) of the two rotamers of the hydroxyamide 1c in the form of a yellow paste.

The two rotamers are obtained in the proportion 65/35, but for convenience, the $^1H$ and $^{13}C$ spectra are described as if the protons or carbons of the minority rotamer had the same intensity as the protons or carbons corresponding to the majority rotamer.

IR (KBr, $cm^{-1}$): 3243, 2973, 2934, 1615, 1443, 1344, 671. NMR $^1H$ (250 MHz, $CDCl_3$) δ (ppm): 8.66 (d, 1H), 8.56 (d, 1H), 8.44 (s, 1H), 8.40 (s, 1H), 7.45-7.43 (m, 4H), 7.36 (d, 2H), 7.29-7.10 (m, 4H), 6.02 (s, 1H), 5.98 (s, 1H), 5.66 (s, 1H), 5.62 (s, 1H), 3.54-3.40 (m, 2H), 3.35-3.24 (m, 2H), 153 (d, 6H), 1.41 (d, 3H), 1.27 (d, 3H), 1.20 (d, 3H), 1.14 (d, 3H), 0.79 (d, 3H), 0.49 (d, 3H). NMR $^{13}C$ (63 MHz, $CDCl_3$) δ (ppm): 169.1, 168.1, 150.8, 150.4, 147.5, 145.6, 145.0, 143.5, 134.9, 134.2, 131.9, 131.8, 126.0, 125.5, 131.2, 130.9, 130.3, 130.0, 129.1, 126.5, 125.1, 124.8, 122.8, 121.8, 75.1, 70.7, 51.5, 51.4, 46.6, 46.4, 20.7, 20.6, 20.5, 20.2, 20.1, 20.0. HR-MS (FAB) for $C_{19}H_{24}N_2O_2Br$: observ. 391.1017; theor. 391.1021.

Step 4: Hydrolysis of the Amide Function and Oxidation of the Alcohol Function of the Hydroxyamide 1c Obtained in Step 3, to Obtain Compound 1d

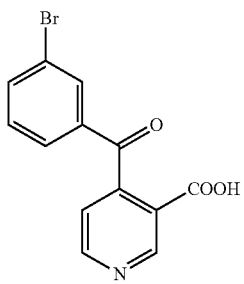

1d

A solution of hydroxyamide 1c (445 mg, 1.2 mmol) in formic acid (85.0 ml, 2.2 mol) is heated to reflux for 24 h. The solvent is evaporated at a reduced pressure, and the residue is taken up in 25 ml of distilled water and then extracted with ethyl acetate (3×20 ml). The organic phases are combined, washed with a saturated sodium bicarbonate solution (2×20 ml), dried over anhydrous sodium sulphate, and then concentrated on a rotating evaporator. The oil obtained is taken up in methanolic ammonia 7 N (85 ml, 3.8 mol). The reaction mixture is stirred in air at ambient temperature for 3 days, and then it is concentrated at a reduced pressure. The residue is dissolved in methanol (30 ml) and 2 M hydrochloric acid is added dropwise until pH=1. The reaction mixture is purified by chromatography in a silica gel column (eluent: dichloromethane/methanol gradient: from 100/0 to 80/20), yielding 312 mg (85%) of the ketoacid 1d in the form of a yellow solid.

$P_f$: 222° C. IR (KBr, cm$^{-1}$): 3419, 3067, 2923, 2852, 1703, 1679, 1605, 1260, 669. NMR $^1$H (300 MHz, DMSO-d6) δ (ppm): 9.11 (s, 1H), 8.68 (d, 1H), 8.25 (s, 1H), 7.75 (d, 1H), 7.68 (s, 1H), 7.49 (d, 1H), 7.41 (t, 1H), 7.26 (d, 1H). NMR $^{13}$C (75 MHz, DMSO-d6) δ (ppm): 194.8, 167.4, 151.7, 150.9, 148.1, 139.8, 132.1, 122.2, 135.4, 131.2, 130.9, 128.0, 120.7. HR-MS (ESI) for $C_{13}H_7NO_3Br$: observ. 303.9624; theor. 303.9609.

Step 5: Synthesis of Compound 1 by Cyclising the Compound 1d Obtained in Step 3

A solution of ketoacid 1d (331 mg, 1.1 mmol) in thionyl chloride (20.0 ml, 300.0 mmol) is stirred at 60° C. in an inert atmosphere for 2 h. The reaction medium is subsequently concentrated at a reduced pressure, and the residue is taken up in dichloromethane and evaporated again. This operation is repeated twice. The residue is finally taken up in acetone (17 ml), and then an aqueous 32% ammonium hydroxide solution (9.2 ml, 3.0 mmol) is added dropwise. The resulting solution is stirred at ambient temperature for 1 h. The reaction medium is concentrated on the rotating evaporator. The residue obtained is purified by chromatography in a silica gel column (eluent: dichloromethane/methanol gradient: from 100/0 to 95/5), yielding 268 mg (80%) of the hemiamidal 1 in the form of a beige powder.

$P_f$: 211° C. IR (KBr, cm$^{-1}$): 3296, 3059, 1693, 1609, 1444, 1291, 647. NMR $^1$H (500 MHz, DMSO-d6) δ (ppm): 9.53 (s, 1H), 8.89 (d, 1H), 8.75 (d, 1H), 7.70 (t, 1H), 7.56 (ddd, 1H), 7.44 (m, 2H), 7.34 (t, 1H), 7.33 (s, 1H). NMR $^{13}$C (126 MHz, DMSO-d6) δ (ppm): 167.5, 158.3, 153.6, 145.2, 143.8, 122.2, 131.7, 131.2, 128.8, 126.5, 125.3, 118.3, 86.6. HR-MS (FAB) for $C_{13}H_{10}N_2O_2Br$: observ. 304.9927; theor. 304.9926.

EXAMPLE 1

Synthesis of Compound 2 of Formula

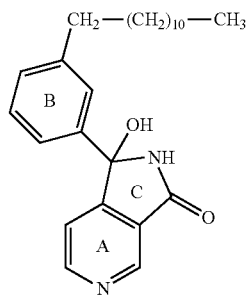

2

An alkylation reaction is carried out starting from compound 1, obtained as described in Preparation 1 above.

n-dodecyl boronic acid (308 mg, 1.44 mmol), diphenylphosphino ferrocene palladium (II) chloride (192 mg, 0.26 mmol), silver (I) oxide (760 mg, 3.20 mmol) and potassium carbonate (542 mg, 4.00 mmol) are added to a solution of the hemiamidal 1 (400 mg, 1.32 mmol) in anhydrous tetrahydrofuran (24 ml) in an inert atmosphere. The tube is hermetically sealed and heated to 80° C. for 48 h. The solution is diluted in dichloromethane (20 ml) and then an $H_2O_2$ (30%)/NaOH (10%) solution is added. This is left for 2 h with stirring. The reaction mixture is extracted with dichloromethane (3×50 ml). The organic phases are combined, dried over anhydrous sodium sulphate and concentrated in a silica gel column (eluent: dichloromethane/methanol gradient: from 100/0 to 90/10), yielding 125 mg (24%) of the hemiamidal 2 in the form of an orange powder.

$P_f$: 108° C. IR (KBr, cm$^{-1}$): 3478, 3413, 3064, 2925, 2851, 1706, 1615, 1280. NMR $^1$H (500 MHz, CDCl$_3$) δ (ppm): 8.82 (s, 1H), 8.62 (d, 1H), 7.40 (s, 1H), 7.37-7.33 (m, 2H), 7.31-7.28 (m, 2H), 7.19 (d, 1H), 5.43 (s large, 1H), 2.60 (t, 2H), 1.59 (q, 2H), 1.30-1.27 (m, 18H), 0.90 (t, 3H). NMR $^{13}$C (126 MHz, CDCl$_3$) δ (ppm): 168.1, 158.3, 153.2, 145.4, 144.0, 138.2, 129.3, 128.8, 125.6, 125.2, 122.7, 117.9, 88.1, 36.0, 31.5, 32.0, 29.9, 29.8, 29.7, 29.6, 29.5, 29.4, 29.3, 22.7, 14.1. HR-MS (FAB) for $C_{25}H_{35}N_2O_2$: observ. 395.2712; theor. 395.2699.

EXAMPLE 2

Synthesis of Compound 3 of Formula

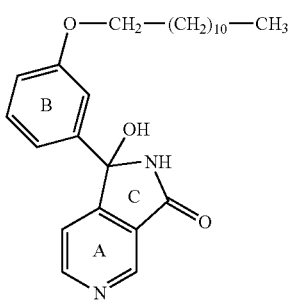

3

Step 1: Synthesis of Compound (3a)

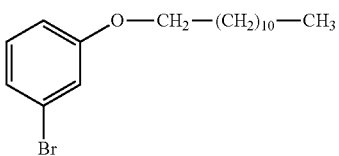

3a

Potassium carbonate (1.20 g, 8.70 mmol) is added to a solution of 3-bromophenol (1.00 g, 5.78 mmol) in anhydrous dimethylformamide (60 ml) in an inert atmosphere at ambient temperature. After 5 minutes of stirring, iododecane (2.57 g, 8.70 mmol) is added. After 18 h, the reaction mixture is filtered. The filtrate is diluted in water (15 ml) and extracted with ethyl acetate (3×30 ml). The organic phases are combined, washed with a saturated sodium chloride solution, and concentrated at a reduced pressure. The residue obtained is purified by chromatography in a silica gel column (eluent: hexane), yielding 1.86 g (94%) of the bromoether 3a in the form of a colourless oil.

IR (film, cm$^{-1}$): 3067, 2924, 2853, 1590, 1573, 1467, 1228, 680. NMR $^1$H (250 MHz, CDCl$_3$) δ (ppm): 7.19-7.07 (m, 3H), 6.85 (dd, 1H), 3.96 (t, 1H), 1.78 (q, 2H), 1.47-1.30 (m, 18H), 0.91 (t, 3H). NMR $^{13}$C (63 MHz, CDCl$_3$) δ (ppm): 160.0, 130.5, 123.5, 117.7, 113.6, 122.8, 68.3, 31.9, 29.7-29.1, 26.0, 22.7, 14.1. MS (DCl/NH$_3$) m/z: 358-360 (M+NH$_4$), 340-342 (M$^+$).

Step 2: Synthesis of Compound 3 by Condensation of 3,4-pyridinedicarboximide and the Compound 3a Obtained in Step 1

Tert-butyl lithium (7 ml, 10.5 mmol, 1.5 M in pentane) is added dropwise to a solution of bromoether 3a (1.90 g, 5.57 mmol) in anhydrous tetrahydrofuran (5.5 ml), in an inert atmosphere at −78° C. After 40 minutes of stirring at −78° C., this solution is added dropwise to a solution of 3,4-pyridinedicarboximide (550 mg, 3.7 mmol) in tetrahydrofuran (22 ml), in an inert atmosphere at −78° C. The reaction mixture is left to return to ambient temperature while stirring. 15 ml of water are added and the reaction mixture is extracted with ethyl acetate (3×25 ml). The organic phases are combined, washed with a saturated aqueous sodium chloride solution (40 ml), dried over anhydrous sodium sulphate and concentrated at a reduced pressure. The oily residue obtained is purified by chromatography in a silica gel column (eluent: dichloromethane/methanol gradient: from 100/0 to 90/10), yielding 346 mg (23%) of a para/meta (3/1) mixture of hemiamidal 3. The mixture is recrystallised in acetone, yielding 3 in the form of a white powder (124 mg, 8%).

$P_f$: 131° C. IR (KBr, cm$^{-1}$): 3413, 3201, 3066, 2923, 2853, 1718, 1615, 1260. NMR $^1$H (500 MHz, DMSO-d6) δ (ppm): 9.46 (s, 1H), 8.86 (d, 1H), 8.72 (d, 1H), 7.42 (dd, 1H), 7.26 (t, 1H), 7.15 (s, 1H), 7.06 (t, 1H), 6.98 (dd, 1H), 6.89 (dd, 1H), 3.94 (t, 2H), 1.69 (q, 2H), 1.39 (m, 2H), 1.30-1.25 (m, 16H), 0.86 (t, 3H). NMR $^{13}$C (126 MHz, DMSO-d6) δ (ppm): 167.5, 159.1, 158.8, 153.4, 145.0, 142.7, 126.5, 131.9, 118.3, 118.0, 114.5, 112.4, 87.6, 67.9, 31.7, 29.5-29.1, 22.5, 26.0, 14.4. HR-MS (ESI) for $C_{25}H_{35}N_2O_3$: observ. 411.2653; theor. 411.2648.

EXAMPLE 3

Synthesis of Compound 4 of Formula

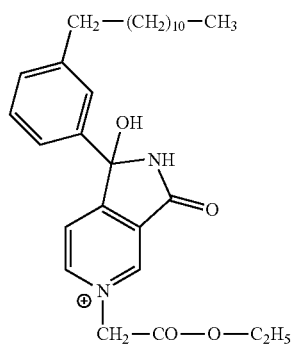

4

Starting from compound 2, obtained as described in Example 1 above, a reaction is carried out to quaternise the pyridine ring.

Ethyl bromoacetate (113 μl, 1.00 mmol) is added dropwise to a solution of hemiamidal 2 (100 mg, 0.25 mmol) in anhydrous tetrahydrofuran (3.2 ml) under reflux in an inert atmosphere. After 48 h, diethyl ether (10 ml) is added, and the precipitate formed is filtered, washed with ether and dried in a vacuum, yielding 142 mg (78%) of the pyridinium salt 4 in the form of a brown powder.

$P_f$: Decomposition. IR (KBr, cm$^{-1}$): 3436, 3150, 2824, 2853, 1718, 1655, 1437, 1217. NMR $^1$H (500 MHz, DMSO-d6) δ (ppm): 10.27 (s, 1H), 9.54 (s, 1H), 9.13 (d, 1H), 8.31 (d, 1H), 7.75 (s, 1H), 6.61 (s, 1H), 7.36-7.34 (m, 2H), 7.25 (d, 1H), 5.69 (s, 2H), 3.79-3.78 (m, 2H), 2.58 (t, 2H), 1.55 (m, 2H), 1.29-1.25 (m, 21H), 0.86 (t, 3H). NMR $^{13}$C (126 MHz, DMSO-d6) δ ppm): 167.2, 166.3, 163.5, 164.5, 150.8, 143.6, 138.4, 130.2, 129.6, 129.2, 126.1, 123.7, 122.3, 88.7, 60.9, 53.7, 35.7, 31.5, 31.7, 29.6-29.2, 22.6, 14.4. HR-MS (ESI) for $C_{29}H_{41}N_2O_4$. observ. 481.3039; theor. 481.3066.

EXAMPLE 4

Synthesis of Compound 5 of Formula

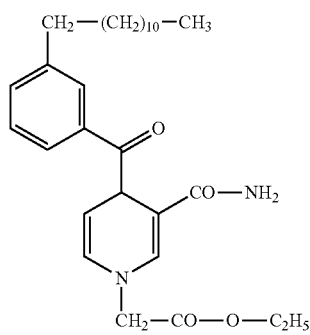

A reaction is carried out starting from compound 4, obtained as described in Example 3 above, to reduce the pyridine ring.

A solution of sodium triacetoxyborohydride (12 mg, 0.053 mmol) in acetic acid (424 µl) is added to a solution of pyridinium salt 4 (20 mg, 0.036 mmol) in ethanol (1.4 ml) in an inert atmosphere at 0° C. After 10 min of stirring, acetone (a few drops) is added, followed by water (10 ml), and the reaction mixture is extracted with dichloromethane (3×10 ml). The organic phases are combined, washed with a saturated sodium bicarbonate solution (2×15 ml), dried over anhydrous sodium sulphate and concentrated at a reduced pressure. The residue obtained is purified by chromatography in a silica gel column (eluent: dichloromethane/methanol gradient: from 100/0 to 90/10), yielding 5.6 mg (33%) of the 1,4-dihydropyridine 5 in the form of an orangey-yellow oil.

NMR $^1$H (300 MHz, $CDCl_3$) δ (ppm): 7.96 (m, 1H), 7.87 (s, 1H), 7.43-7.38 (m, 2H), 7.13 (s, 1H), 5.89 (d, 1H), 5.29 (s large, 2H), 5.11 (d, 1H), 4.91 (dd, 1H), 4.26 (q, 2H), 3.98 (s, 2H), 2.67 (t, 2H), 1.33 (t, 3H), 1.29-1.25 (m, 20H), 0.90 (t, 3H). NMR $^{13}$C (126 MHz, $CDCl_3$) δ (ppm): 198.8, 169.4, 168.9, 143.5, 138.4, 135.3, 133.4, 128.5, 129.7, 129.1, 126.7, 102.8, 102.5, 61.8, 54.7, 44.1, 35.9, 31.9, 31.6, 29.7-29.3, 22.7, 14.2, 14.1. HR-MS (ESI) for $C_{29}H_{43}N_2O_4$: observ. 483.3215; theor. 483.3223.

EXAMPLES 5-7

Synthesis of 1-(3-octyloxyphenyl)-1-hydroxy-1,2-dihydro-3H-pyrrolo[3,4-c]pyridin-3-one (6), 1-(2-dodecyloxyphenyl)-1-hydroxy-1,2-dihydro-3H-pyrrolo[3,4-c]pyridin-3-one (7) and 1-(3-octodecyloxyphenyl)-1-hydroxy-1,2-dihydro-3H-pyrrolo[3,4-c]pyridin-3-one (8)

Step 1: Synthesis of 1-bromo-3-octyloxybenzene (6a), 1-bromo-2-decyloxybenzene (7a) and 1-bromo-3-octadecyloxybenzene (8a)

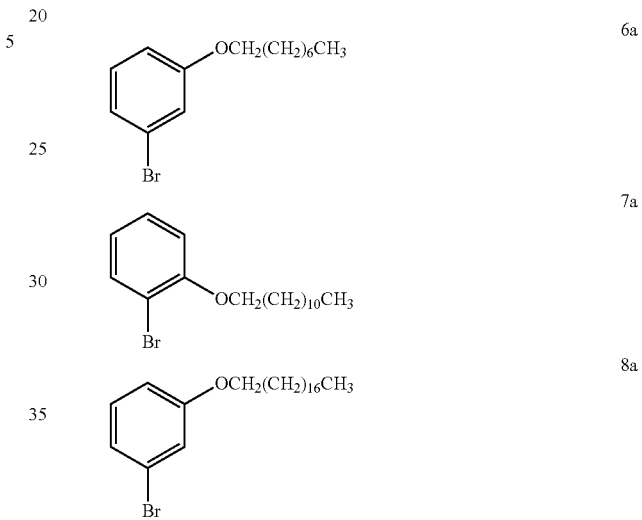

Potassium carbonate (1.2 g; 8.7 mmol) is added to a solution of bromophenol (1.00 g; 5.8 mmol) in dimethylformamide (60 ml), the system is left in an inert atmosphere for 5 minutes with stirring, and subsequently 1-iodoalkane (8.67 mmol) is introduced. After 12 h of reaction at ambient temperature, 40 ml of water are added, the reaction medium is extracted with ethyl acetate (3×30 ml), the organic phases are recovered, dried over anhydrous sodium sulphate and concentrated in a vacuum. The residue obtained is purified by chromatography in a silica gel column (eluent: cyclohexane), yielding the desired compound.

Compound 6a: 87% IR (cm$^{-1}$): 3067, 2924 (CH), 2854, 1589 (C=C), 1466, 1243, 1227 (C—O), 1028, 860, 762, 679 (C—Br). NMR $^1$H (250 MHz, $CDCl_3$) δ (ppm): 7.20 (m, 3H); 6.90 (dt, J=1.4 Hz and 8.8 Hz, 1H); 3.90 (t, 2H, J=6.5 Hz); 1.87 (m, 2H); 1.53 (m, 10H); 0.99 (t, 3H, J=4.9 Hz). NMR $^{13}$C (63 MHz, $CDCl_3$) δ (ppm): 160.0 (C); 130.5 (CH); 123.6 (CH); 122.8 (C); 117.8 (CH); 113.6 (CH); 68.3 (CH2); 31.9 (CH2); 29.4 (CH2); 29.3 (CH2); 26.0 (CH2); 22.7 (CH2); 14.1 (CH3). MS (DCl/$CH_4$) m/z: 285/287 (M+H$^+$). HR-MS: for $C_{14}H_{22}OBr$: theoretical mass: 285.0852; calculated mass: 285.0854.

Compound 7a: 92% IR (cm$^{-1}$): 2922 (CH), 2853, 1588 (C=C), 1277, 1247 (C—O), 1051, 1030, 744, 665 (C—Br). NMR $^1$H (500 MHz, $CDCl_3$) δ (ppm): 7.57 (dd, J=7.9 Hz and 1.6 Hz, 1H); 7.28 (ddd, J=1.6 Hz, 7.4 Hz and 7.4 Hz, 1H); 6.91 (dd, J=1.4 Hz and 8.2 Hz, 1H); 6.84 (td, J=1.4 Hz and 7.7

Hz, 1H); 4.05 (t, J=6.6 Hz, 2H); 1.87 (dt, J=6.6 Hz and 15.2 Hz, 2H); 1.60-1.30 (m, 18H); 0.89 (t, J=6.2 Hz, 3H). NMR $^{13}$C (126 MHz, CDCl$_3$) δ (ppm): 155.5 (C); 133.3 (CH); 128.4 (CH); 121.6 (CH); 113.2 (CH); 112.3 (C); 69.2 (CH2); 32.0 (CH2); 29.7-22.7 (9×CH2); 14.1 (CH3). MS (DCl/CH4) m/z: 342.4 (M+H$^+$). HR-MS: for C$_{18}$H$_{30}$OBr: theoretical mass: 341.1464; calculated mass: 341.1480.

Compound 8a: 82% IR (cm$^{-1}$): 2915 (C—H), 2847, 1597 (C=C), 1471, 1241 (C—O), 1021, 861, 782, 683 (C—Br). NMR $^1$H (250 MHz, CDCl$_3$) δ (ppm): 7.18 (m, 3H, H6); 6.87 (td, J=0.9 Hz, 1.4 Hz and 7.9 Hz, 1H); 3.98 (t, J=6.5 Hz, 2H); 1.85 (t, J=6.5 Hz, 2H); 1.49 (m, 30H); 0.93 (t, J=6.1 Hz, 3H). NMR $^{13}$C (63 MHz, CDCl$_3$) δ (ppm): 160.0 (C); 130.5 (CH); 123.5 (CH); 123.0 (C); 117.8 (CH); 113.5 (CH); 68.3 (CH2); 32.0 (CH2); 29.8-22.7 (15×CH2); 14.1 (CH3). MS (DCl/CH4) m/z: 425.2/427.2 (M+H$^+$). HR-MS: for C$_{24}$H$_{42}$OBr: theoretical mass: 425.2408; calculated mass: 425.2419.

Step 2: Synthesis of Compounds 6-8

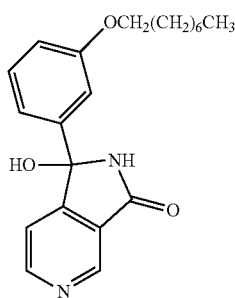

6

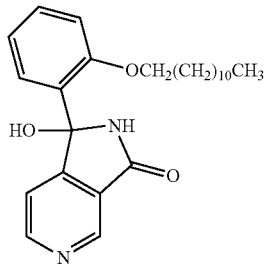

7

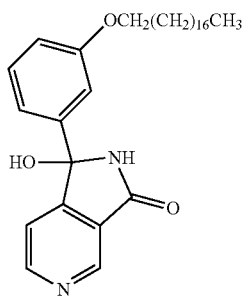

8

1.5 M tert-butyllithium (1.5 ml; 2.42 mmol) is added dropwise to an appropriate, suitably substituted solution of bromoether obtained in accordance with step 1 (1.21 mmol) in dry tetrahydrofuran (7.5 ml) in an inert atmosphere at −78° C. After this addition, the temperature is increased to −50° C. for 30 minutes. The handling temperature is then reduced to −78° C. again and this solution is added to 3,4-pyridinedicarboximide (180 mg, 1.21 mmol) in anhydrous tetrahydrofuran (12 ml) at −78° C. The reaction mixture is stirred for one hour at −50° C. Then, the reaction is treated with a saturated ammonium chloride solution (10 ml) and the reaction medium is extracted with ethyl acetate (3×8 ml). The organic phases are recovered, dried over sodium sulphate and concentrated in a vacuum. The white powder obtained is purified by chromatography in a silica gel column (eluent: dichloromethane/methanol gradient: 100/0 to 93/7), yielding a mixture of para/meta compounds. The para product A is recovered cleanly after 3 days of recrystallisation in acetone.

Compound 6: 28% IR (cm$^{-1}$): 3350 (NH, OH), 2918 (C—H), 2849, 1714 (C=O), 1613 (C=C), 1465 (C—H), 1340, 1207, 1067, 727. NMR $^1$H (500 MHz, MeOD) δ (ppm): 8.93 (s, 1H); 8.73 (d, J=5.0 Hz, 1H); 7.48 (dd, J=5.1 Hz and 0.8 Hz, 2H); 7.29 (t, 1H, J=8.0 Hz); 7.18 (t, 1H, J=2.0 Hz); 7.07 (d, 1H, J=8.0 Hz); 6.91 (dd, J=7.5 and 1.8 Hz); 4.0 (m, 2H); 1.80 (q, J=6.5 Hz, 2H); 1.49 (m, 18H); 0.93 (t, J=6.8 Hz, 3H). NMR $^{13}$C (126 MHz, MeOD) δ (ppm): 168.4 (C); 159.5 (CH); 159.4 (C); 152.5 (CH); 144.4 (CH); 141.0 (C); 129.4, 117.2, 114.3, 111.6 (4×CH); 118.0 (C); 87.7 (C); 67.6 (CH2); 31.5 (CH2); 29.0-28.9 (3×CH2); 25.7 (CH2); 22.2 (CH2); 13.0 (CH3).

Compound 7: 31% P$_f$=132° C. IR (cm$^{-1}$): 3199 (OH, NH), 3061 (C—H), 2920, 2851, 1708 (C=O), 1619 (C=C), 1284, 1243, 1073, 1045, 1022. NMR $^1$H (500 MHz, MeOD) δ (ppm): 8.90 (d, J=1.1 Hz, 1H); 8.69 (d, J=5.3 Hz, 1H); 8.07 (dd, J=1.8 Hz and 7.8 Hz, 1H); 7.37 (ddd, J=1.8 Hz, 7.5 Hz and 8.1 Hz); 7.32 (dd, J=1.4 Hz, and 5.1 Hz, 1H); 7.05 (dt, J=1.0 Hz and 7.7 Hz, 1H); 6.88 (dd, J=0.7 Hz and 8.3 Hz, 1H); 3.74 (dt, J=6.3 Hz and 9.2 Hz, 1H); 3.56 (dt, J=6.3 Hz and 9.1 Hz, 1H); 1.35-1.20 (m, 18H); 0.92 (t, J=6.8 Hz, 3H). NMR $^{13}$C (126 MHz, MeOD) δ (ppm): 169.1 (C); 160.5 (C); 155.9 (C); 152.1 (CH); 143.8 (CH); 130.2 (CH); 128.5 (C); 127.8 (CH); 125.8 (CH); 119.8 (CH); 117.3 (CH); 111.6 (CH); 85.6 (C); 67.8 (CH2); 31.7-25.6 (9×CH2); 22.4 (CH2); 13.1 (CH3). MS (ESI/CH$_3$OH)): 433 (M+Na$^+$); 411 (M+H$^+$); 393 (M+H$^+$—H$_2$O). HR-MS: for C$_{25}$H$_{35}$N$_2$O$_3$: theoretical mass: 411.2681; calculated mass: 411.2648.

Compound 8: 23% P$_f$: 113° C. IR (cm$^{-1}$): 3141 (NH, OH), 3059, 2920 (C—H), 2851, 1708 (C=O), 1607 (C=C), 1578, 1286, 1258, 1030, 700. NMR $^1$H (500 MHz, MeOD) δ (ppm): 8.93 (s, 1H); 8.73 (d, J=5.4 Hz, 1H); 7.46 (d, J=0.95 Hz and 5.1 Hz, 1H); 7.29 (t, J=8.0 Hz, 1H); 7.17 (m, 1H); 7.08 (dd, J=8.8 Hz and 1.7 Hz, 1H); 6.91 (dt, J=8.3 Hz, other J not measurable, 1H); 3.99 (m, 2H); 1.78 (q, J=6.7 Hz, 2H); 1.48-1.31 (m, 30H); 0.92 (t, J=6.8 Hz, 3H). NMR $^{13}$C (125 MHz, MeOD) δ (ppm): 1 quaternary carbon absent, 168.5 (C); 159.5 (C); 159.4 (C); 152.6 (CH); 144.5 (CH); 141.1 (C); 129.4 (CH), 126.4 (C); 117.9 (CH), 117.4 (C); 114.5 (CH); 111.8 (CH); 67.9 (C); 31.6 (CH2); 29.3-28.9 (13×CH2); 25.7 (CH2); 22.2 (CH2); 12.9 (CH3). MS (ESI/CH$_3$OH)): 495.5

(M+H⁺). HR-MS: for $O_{31}H_{47}N_2O_3$: theoretical mass: 495.3618; calculated mass: 495.3587.

EXAMPLE 8

Synthesis of 1-[3-(dodecylthio)phenyl]-1-hydroxy-1,2-dihydro-3H-pyrrolo[3,4-c]pyridin-3-one (9)

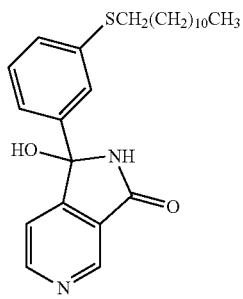

Step 1: Synthesis of 1-bromo-3-(dodecylthio)benzene (9a)

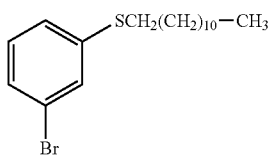

Potassium carbonate (1.6 g; 11.8 mmol) is added to a solution of 3-bromobenzene thiol (1.50 g; 7.9 mmol) in dimethylformamide (90 ml) and the system is left in an inert atmosphere for 5 minutes with stirring, and subsequently 1-iododecane (3.5 g; 11.8 mmol) is introduced. After 16 h of reaction at ambient temperature, 50 ml of water are added, the reaction medium is extracted with ethyl acetate (3×30 ml), and the organic phases are recovered, dried over sodium sulphate and concentrated in a vacuum. The product obtained 9a, in the form of a colourless oil (4.5 g), is purified by chromatography in a silica gel column (eluent: cyclohexane), yielding 1.9 g (70%).

IR (cm⁻¹): 2921 (C—H), 2851 (C—H), 1576 (C=C), 1458 (C—S), 1068, 753, 676 (C—Br); NMR ¹H (250 MHz, CDCl₃) δ (ppm): 7.46 (dd, 1H, J=6.7 Hz and 1.6 Hz); 7.23-7.32 (m, 2H, H4); 7.16 (dd, 1H, J=12.0 Hz and 7.8 Hz); 2.97 (t, 2H, J=7.2 Hz); 1.65 (t, 2H, J=7.3 Hz); 1.29 (m, 18H); 0.91 (t, J=6.6 Hz, 3H). NMR ¹³C (63 MHz, CDCl₃) δ (ppm): 139.8 (C); 130.7 (CH); 130.0 (CH); 128.5 (CH); 126.9 (C); 122.8 (C); 33.3 (CH2); 31.9 (CH2); 29.7-28.8 (8×CH2); 22.7 (CH2); 14.1 (CH3). MS (DCl/CH₄) m/z: 357 (M+H⁺); 385 (M+C₂H₅⁺). HR-MS: for $C_{18}H_{30}SBr$: theoretical mass: 357.1236; calculated mass: 357.1252.

Step 2: Synthesis of Compound (9)

n-butyllithium 1.5 M (1.4 ml; 3.36 mmol) is added dropwise to a solution of bromobenzene 9a (1.00 g; 2.8 mmol) in dry tetrahydrofuran (18 ml) in an inert atmosphere at −78° C. After this addition, the temperature is increased to −50° C. for 30 minutes. The handling temperature is then reduced to −78° C. again and this solution is added to 3,4-pyridinedicarboximide (166 mg, 1.12 mmol) in anhydrous tetrahydrofuran (22 ml). The reaction mixture is stirred for one hour at −50° C. Then, the reaction is treated with a saturated ammonium chloride solution (30 ml) and the reaction medium is extracted with ethyl acetate (3×20 ml). The organic phases are recovered, dried over sodium sulphate and concentrated in a vacuum. The white powder obtained (720 mg) is purified by chromatography in a silica gel column (eluent: dichloromethane/methanol gradient: 100/0 to 93/7), yielding 128 mg (48%) of the para/meta mixture of compounds. The para product is recovered (32.3 mg; 28%) after 3 days of recrystallisation in acetone. This recrystallisation product is still contaminated with 23% meta compound.

$P_f$=86° C. IR (cm⁻¹): 3159 (NH, OH), 2917 (C—H), 2848 (C—H), 2424, 1698 (C=O), 1614 (C=C), 1547, 1464 (C—S), 1347, 1067, 964 (C=C), 784, 698. NMR ¹H (250 MHz, MeOD) δ (ppm): 8.94 (s, 1H); 8.74 (d, 1H, J=5.0 Hz); 7.56 (s, 1H); 7.46 (d, 1H, J=4.6 Hz, 1H); 7.31 (m, 3H, H14); 2.96 (t, 2H, J=7.0 Hz); 1.64 (m, 2H); 1.42 (m, 18H); 0.94 (t, 3H, J=6.0 Hz). NMR ¹³C (126 MHz, MeOD) δ (ppm): 159.0 (C); 152.7 (CH); 150.0 (C); 144.4 (CH); 144.0 (C); 140.0 (C); 138.0 (C); 128.9 (CH), 128.4 (CH); 125.2 (CH), 122.5 (CH); 118.0 (CH, C5); 88.0 (C), 71.0 (CH2); 32.6 (CH2); 31.7 (CH2); 29.4-28.4 (CH2); 22.3 (CH2); 13.0 (CH3, C29).

MS (ESI/CH₃OH)): 449.2 (M+Na⁺); 427.3 (M+H⁺). HR-MS: for $C_{25}H_{35}N_2O_2S$: theoretical mass: 411.2681; calculated mass: 411.2648.

EXAMPLE 9

Synthesis of 1-(3-dodecyloxyphenyl)-1-methoxy-1,2-dihydro-3H-pyrrolo[3,4-c]pyridin-3-one (10)

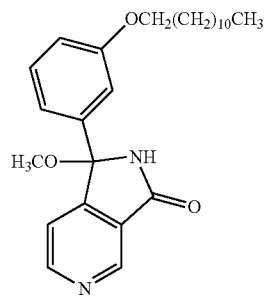

0.5 ml of thionyl chloride are added to a solution of 3 (100 mg; 0.44 mmol) in methanol dried on a molecular sieve (6 ml). The mixture is brought to reflux in an argon atmosphere for 16 h. The heating is halted, and when the medium reaches ambient temperature, it is treated with a saturated sodium bicarbonate solution (5 ml) and extracted with ethyl acetate (3×8 ml). The organic phases are recovered, dried over sodium sulphate and concentrated in a vacuum, yielding 93 mg (89%) yellow oil.

IR (cm⁻¹): 2922 (C—H), 2852, 1726 (C=O), 1603 (C=C), 1438, 1287 (C—O), 1051, 698.

NMR ¹H (250 MHz, CDCl₃) δ (ppm): 9.08 (s, 1H), 8.78 (s, 1H), 7.39-6.89 (m, 6H), 3.97 (t, J=6.4 Hz, 2H), 3.17 (s, 3H), 1.79 (t, J=5.5 Hz, 2H), 1.45-1.28 (m, 18H), 0.91 (t, J=5.9 Hz, 3H). NMR ¹³C (63 MHz, CDCl₃) δ (ppm): 168.1 (C); 159.6 (CH); 154.9 (C); 153.2 (CH); 146.0 (CH); 139.7 (2×C); 130.0 (CH); 118.0 (C) 117.4 (CH), 114.8 (CH); 112.1 (CH); 91.9 (C); 68.2 (CH2); 50.9 (CH3); 31.9 (CH2); 29.6-29.3 (6×CH2); 26.0 (CH2); 22.7 (CH2); 14.1 (CH2); 1.0 (CH3).

MS (ESI/CH$_3$OH)) m/z: 425.6 (M+H$^+$). HR-MS: for C$_{26}$H$_{37}$N$_2$O$_3$: theoretical mass: 425.2847; calculated mass: 425.2804.

The following compounds were synthesised by applying or adapting methods disclosed above using appropriate starting materials and reagents:

| Ex. | A | B | R1 | R2 | R3 |
|---|---|---|---|---|---|
| 1 | pyridine (attachments at 2,3 positions) | phenyl–C$_{12}$H$_{25}$ | together form a single bond | | OH |
| 2 | pyridine | phenyl–OC$_{12}$H$_{25}$ | together form a single bond | | OH |
| 3 | N-substituted pyridinium Br$^-$, N–CH$_2$–C(=O)–OC$_2$H$_5$ | phenyl–C$_{12}$H$_{25}$ | together form a single bond | | OH |
| 4 | N-substituted dihydropyridine, N–CH$_2$–C(=O)–OC$_2$H$_5$ | phenyl–C$_{12}$H$_{25}$ | H | together form a *=O group | |
| 5 | pyridine | phenyl–OC$_8$H$_{17}$ | together form a single bond | | OH |
| 6 | pyridine | phenyl–OC$_{12}$H$_{25}$ | together form a single bond | | OH |
| 7 | pyridine | phenyl–OC$_{18}$H$_{37}$ | together form a single bond | | OH |
| 8 | pyridine | phenyl–SC$_{12}$H$_{25}$ | together form a single bond | | OH |
| 9 | pyridine | phenyl–OC$_{12}$H$_{25}$ | together form a single bond | | OCH$_3$ |

-continued structure: B ring with R3, R22, NHR1 attached to central carbon bonded to A ring with C=O

| Ex. | A | B | R1 | R2 | R3 |
|---|---|---|---|---|---|
| 10 | pyridine | phenyl-O-allyl | together form a single bond | | OH |
| 11 | pyridine | phenyl-OH | together form a single bond | | OH |
| 12 | pyridine | phenyl-C₈H₁₇ | together form a single bond | | OH |
| 13 | pyridine | biphenyl-C₉H₁₉ | together form a single bond | | OH |
| 14 | N-substituted pyridinium (CH₂-C(=O)-OC₂H₅) Br⁻ | phenyl-OC₁₂H₂₅ | together form a single bond | | OH |
| 15 | N-substituted pyridinium (CH₂-C(=O)-OC₃H₆OH) Br⁻ | phenyl-OC₁₂H₂₅ | together form a single bond | | OH |
| 16 | N-substituted dihydropyridine (CH₂-C(=O)-OC₂H₅) | phenyl-OC₁₂H₂₅ | H | together form a *=O group | |
| 17 | N-substituted dihydropyridine (CH₂-C(=O)-OC₃H₆OH) | phenyl-OC₁₂H₂₅ | H | together form a *=O group | |

In the table above, the asterisks (*) denote the positions of attachments and substitutions of the rings A and B.

EXAMPLE 18

Demonstration of the Inhibitory Effect of the Claimed Compounds on InhA Activity 1—Preparation of InhA Enoylreductase The InhA protein was expressed in *E. coli* after cloning the inhA gene in a plasmidic vector of the pET type. Growing the resulting strain and inducing expression of the inhA gene with 1 mM IPTG (isopropyl β-D-thiogalactoside) leads to the production of water-soluble InhA protein at approximately 28.5 KDa (28,368 Da) (monomeric) which is purified by standard protein purification techniques. The enzyme is present in the form of a tetramer in solution and is kept in 50 mM Hepes buffer, 50% glycerol at −20° C.

2—Evaluation of the Activity of InhA Enoylreductase

The InhA enoylreductase activity is monitored by UV spectrometry, by monitoring the disappearance of the signal of the reduced cofactor NADH at 340 nm as a function of time. The percentage inhibition is calculated by subtracting from 100 the ratio of the initial speeds (V) measured during kinetics with and without inhibitor, multiplied by 100:% inhibition=100−($V_{inhib}/V_{blank}$*100). The initial speed is measured by drawing the tangent to the curve DO=f(time) at time zero.

3—InhA Enoylreductase Activity Inhibition Test

The enzymatic reaction is carried out in a final volume of 100 μl (in a quartz vessel, optical path 1 cm). The absorption of each reaction mixture is determined with a UVIKON 293 spectrophotometer (Bio-Tek Kontron Instruments) connected to a thermostatically controlled bath which makes it possible to maintain the temperature of the vessel at 25° C. A baseline is produced during preincubation immediately before measurements begin. The measurements are carried out over 3 min after a preincubation of 5 min or 2 h.

The preincubation is carried out in 90 μl (total volume) of a solution of PIPES buffer 30 mM, NaCl 150 mM, pH=6.8 at 25° C. containing 100 nM of InhA, 100 μM, 20 μM or 10 μM of the compound to be tested (or 500 nM of the pool of INH-NAD adducts constituting the control inhibitors) and 200 μM of NADH. After 5 min or 2 h of preincubation, the addition of 35 μM of the substrate 2-trans-decenoyl-CoA initiates the reaction. Alternatively, the preincubation is carried out in 80 μl (total volume) of a solution of PIPES buffer 30 mM, NaCl 150 mM, pH=6.8 at 25° C. containing 100 nM of InhA and 100 μM, 20 μM or 10 μM of the compound to be tested (or 500 nM of the pool of adducts constituting the control inhibitors). After 5 min or 2 h of preincubation, the addition of 200 μM of NADH and 35 μM of 2-trans-decenoyl-CoA initiates the reaction.

4—Results

The results obtained show that some derivatives of the molecular family according to the invention exhibit an efficacious inhibitory effect on the operation of InhA, close to that of the active metabolites of isoniazide (obtained by biomimetic synthesis in the form of a mixture of adducts). The InhA inhibition percentages as a function of the inhibitor concentration and for a preincubation time of 5 min (or *2 h) are shown below:

| | | |
|---|---|---|
| Reference mixture of INH-NAD adducts: | 10 μM | 92% |
| Compound of example 2 | 100 μM | 41% (* 80%) |
| | 100 μM | 91% |
| Compound of example 3 | 10 μM | 19% |
| Compound of example 4 | 10 μM | 25% |

EXAMPLE 19

Demonstration of the Growth Inhibition of the Compounds According to the Invention on Different Bacterial Strains: Case of *Mycobacterium smegmatis*

1—Preparation of the Bacterial Suspension of *Mycobacterium smegmatis*

The strain *Mycobacterium smegmatis* mc$^2$155 ($R_0$) is cultivated in a culture medium of Middelbrook 7H9(Difco)+ glycerol 0.2%+0.05% Tween 80 at 37° C. with stirring (200 rpm) to avoid the formation of a bacterial film. After 3 days, the $R_0$ culture is left to rest for 10 min, in which time the largest aggregates settle. The supernatant is removed to start a new culture $R_1$, in the same conditions, seeded at ¹⁄₁₀₀. After 3 days of stirring at 37° C. and 10 min of rest, the supernatant is removed. The optical density of the bacterial suspension is measured at 650 nm and set to a value of between 0.002 and 0.003 by dilution in the culture medium (without Tween 80), and this is $R_2$.

2—Evaluation of the Growth of the Bacterial Suspension of *Mycobacterium smegmatis*

The antimycobacterial activity is evaluated by MTT reduction colorimetric tests (3-(4,5-dimethylthiazol-2-yl)-2,5-diphenyl-2H-tetrazolium bromide) on the strain *M. smegmatis* mc$^2$155. Once the bacteria have been allowed to develop normally, the yellow tetrazolium salt (MTT) is reduced and changes colour, becoming purple. By contrast, if the growth of the bacteria is completely inhibited by one of our compounds, the reduction cannot take place and the solution remains yellow. Reading the optical density at 570 nm makes it possible to observe the formation of purple, reduced MTT fromazan The percentage inhibition is calculated by subtracting from 100 the ratio of the DO measured with and without inhibitor, multiplied by 100: 100−($DO_{inh}/DO_{tem}$*100).

3—Inhibitive Activity of the Products to be Tested on the Growth of the Bacterial Suspension of *Mycobacterium smegmatis*

The tests are carried out on 96-well NUNC microplates (Merk-eurolab). Each product is tested over a concentration range starting at 5 mM by carrying out successive dilutions of two by two. Each well contains 100 μl of compound in solution in the culture medium (7H9+0.2% Gro with 1% (v/v) final DMSO). Subsequently, 100 μl of bacterial suspension $R_2$ are added. The plate is sealed using parafilm and incubated at 37° C. After 24 hours of incubation, 50 μl of a 1 mg/ml solution of MTT are added to each well. After 3 hours of incubation at 37° C., 100 μl of lysis buffer are added to each well and the plate is left with stirring at ambient temperature until the solution is fully homogeneous.

The optical density is measured at 570 nm with a μQuant microplate spectrophotometer, Bio-tek Instruments, Inc.

4—Results

The results obtained show that some derivatives of the family according to the invention exhibit $CI_{50}$ values (concentration corresponding to 50% inhibition) on the growth of the strain *Mycobacterium smegmatis* which are better than those observed for the isoniazide used as a reference.

isoniazide (INH)
7.8 uM

[structure] 4.5 uM

[structure] 3.2 uM

[structure] 5.4 uM

CI$_{50}$ of isoniazide and 3 compounds on the bacterial strain Mycobacterium smegmatis.

EXAMPLE 19

Demonstration of the Growth Inhibition of the Compounds According to the Invention on Different Bacterial Strains: Case of *Corynebacterium qlutamicum*

The CI$_{50}$ of the compounds according to the invention on the bacterial strain *C. glutamicum* and for the control INH was determined.

As expected, INH does not exhibit any activity on *C. glutamicum* at 5 mM.

The compounds according to the invention, specifically described hereinafter, are able to inhibit the growth of the bacterium *C. glutamicum* at a CI$_{50}$ less than or equal to 10 µM. These results suggest that the compounds cited below have another molecular target in addition to InhA.

In fact, the bacteria in this strain exhibit the distinctive feature of not having a FAS-II elongation cycle in the biosynthesis of fatty acids. There is no InhA equivalent in *C. glutamicum*. The compounds according to the invention which act on this strain of bacteria therefore also have a target other than the FASS-II system.

Preparation of the Bacterial Suspension of *C. glutamicum*

The *Corynebacterium glutamicum* strain is cultivated in a BHI (Brain-Heart Infusion) medium at 30° C. with stirring at 200 rpm. The DO of the culture is measured directly and set to a value of 0.002-0.003 by dilution in the LB culture medium. *C. glutamicum* also grows in the LB medium, and this is used instead of BHI, which is strongly coloured and interferes with the DO reading at 570 nm.

Preparation of the Solutions of Compounds to be Tested

The concentration ranges tested on *C. glutamicum* are shown in the table.

| Compounds | Concentration range tested |
|---|---|
| INH | 5 mM to 2.4 µM |
| A | 156 µM to 2.4 µM |
| Example 2 | 312 µM to 4.9 µM |
| Example 4 | 78 µM to 1.2 µM |
| Example 5 | 39 µM to 0.6 µM |

The stock solutions are prepared in DMSO at a concentration 100 times greater than the highest concentration to be tested.

Evaluation of the Growth of the Bacterial Suspension of *C. glutamicum*

The test is carried out in the same way as the test on *M. smegmatis*.

The tests are carried out on 96-well NUNC microplates (Merck-eurolab). All the concentrations were tested at least twice.

Each well contains 100 µl of compound in solution in the culture medium (LB with 1% final DMSO). Subsequently, 100 µl of bacterial suspension having DO 0.002 at 650 nm are added.

The plate is sealed using parafilm and incubated at 30° C. for *C. glutamicum*. After two hours of incubation, 50 µl of a 1 mg/ml solution of tetrazolium salt (MTT) are added to each well. After one hour of incubation at 30° C. for *C. glutamicum*, 100 µl of lysis buffer are added to each well and the plate is left with stirring at ambient temperature until the solution is fully homogeneous.

The optical density is measured at 570 nm with a µQuant 96-well microplate spectrophotometer, Bio-tek Instruments, Inc.

Results

The $CI_{50}$ values of isoniazide and 4 compounds on the bacterial strain *Coryne glutamicum* are shown below:

Compound A: Example 2: Example 4:

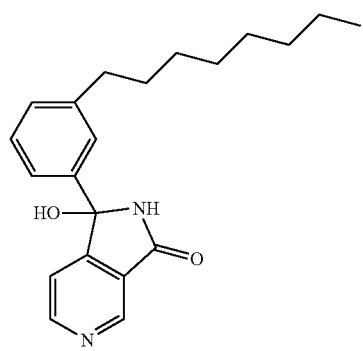

$CI_{50} = 11.5 \mu M +/- 0.1$

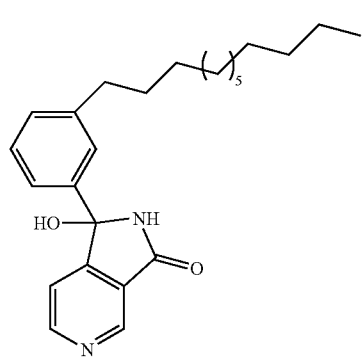

$CI_{50} = 2.3 \mu M +/- 0.3$

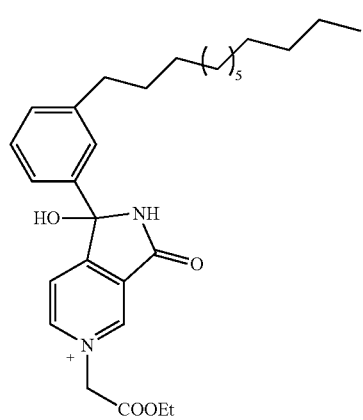

$CI_{50} = 1.56 \mu M +/- 0.05$

EXAMPLE 5

Isoniazide $CI_{50} > 5$ mM

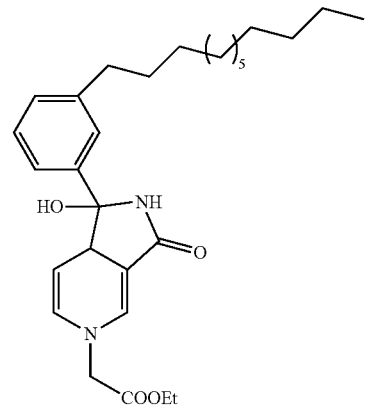

$CI_{50} = 7.1 \mu M +/- 0.9$

The results obtained demonstrate the ability of the compounds according to the invention to inhibit the growth of *C. glutamicum* (a bacterial strain without an InhA equivalent), and this suggests that other targets may exist.

The invention claimed is:

1. Compounds of general formula (I):

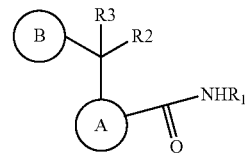

in which:

the cycle

represents a 6-membered aromatic optionally comprising one or more nitrogen atoms, said nitrogen atom(s) optionally being substituted by an optionally substituted tetrahydrofuran group, such as 2-hydroxymethyl-tetrahydrofuran-3,4-diol; or by a —CH$_2$-E group, wherein E represents an electron-attracting group such as —CONRR'; —CO—SR; —CO—Oalkyl; —CO—Oalkyl-OH; —O-alkyl-OAc; phenyl substituted for example by a CN or NO$_2$ group; wherein R and R' are the same or different and independently represent a hydrogen atom or an alkyl group;

and/or wherein said nitrogen atom(s) may be in the form of pyridinium salts, the counter ion being the anion of a halogen atom, such as bromide;

(B)

represents a 5-to-10-membered mono- or bicyclic aryl group or heteroaryl group comprising one to three N atoms, substituted by one or more groups selected from the groups —OH; —($C_5$-$C_{20}$)alkyl; —O($C_2$-$C_{20}$)alkyl; —S(O)$_p$alkyl wherein p=0, 1 or 2; alkenyl; alkynyl; —Oalkenyl; —C(=)O-alkyl; —C(=O)-alkenyl; phenyl substituted by an alkyl group; cycloalkyl optionally substituted by an alkyl group, wherein (B)

is substituted in the ortho or meta position;

R1 represents a hydrogen atom or an alkyl group and R2 and R3 together form an =O group;

or alternatively

R3 represents an —OH or —Oalkyl group and R2 forms, together with R1, a single bond;

the groups —C(=O)NHR1 and C(R3)(R2)- being understood to be located in two adjacent positions on the ring (A);

in the form of a base or an acid addition salt, as well as in the form of a pharmaceutically acceptable hydrate or solvate.

2. Compounds according to claim 1, wherein in the general formula (I), (A)

is a phenyl, pyridine, pyrazine or dihydropyridine ring.

3. Compounds according to claim 1, wherein in the general formula (I), (A)

represents a dihydropyridine or pyridine group, optionally substituted by a group selected from the groups —$CH_2$—CO—Oalkyl; —$CH_2$—CO—Oalkyl-OH; —$CH_2$—O-alkyl-OAc, and/or optionally in the form of a pyridinium halide.

4. Compounds according to claim 1, wherein in the general formula (I), (B)

is a phenyl ring substituted by a —OH, ($C_5$-$C_{20}$)alkyl, O($C_5$-$C_{20}$)alkenyl, O($C_5$-$C_{20}$)alkyl or —S(O)$_p$alkyl group wherein p=0, 1 or 2.

5. Compounds according to claim 1, wherein in the general formula (I), R3=OH or —Oalkyl and R1 and R2 together form a single bond.

6. Compounds according to claim 1, wherein in the general formula (I), R3 and R2 form an =O group and R1 represents a hydrogen atom.

7. Compounds according to claim 1, wherein in the general formula (I):

(A)

represents a dihydropyridine group, optionally substituted by a group selected from —$CH_2$COOalkyl, —$CH_2$COOalkylOH;

(B)

represents a phenyl group, substituted in the meta position, by a group selected from the groups $C_5$-$C_{20}$ alkyl, —O($C_2$-$C_{20}$)alkyl, —Oalkenyl, —OH, phenyl optionally substituted by alkyl;

R1 and R2 together form a single bond and R3=OH, or R1=H and R2 and R3 together form an =O group; in the form of a base or an acid addition salt, as well as in the form of a pharmaceutically acceptable hydrate or solvate.

8. Compounds according to claim 1, selected from the following compounds:

1-(3-dodecylphenyl)-1-hydroxy-1,2-dihydropyrrolo[3,4-c]pyridin-3-one;

1-(3-dodecyloxyphenyl)-1-hydroxy-1,2-dihydropyrrolo[3,4-c]pyridin-3-one;

1-(3-dodecylphenyl)-5-[2-(ethyloxy)-2-oxoethyl]-1-hydroxy-3-oxo-1,2-dihydropyrrolo[3,4-c]pyridinium bromide;

ethyl 3-aminocarbonyl-[4-(3-dodecylbenzoyl)-1,4-dihydro-pyridin-1-yl] acetate;

1-(3-octyloxyphenyl)-1-hydroxy-1,2-dihydro-3H-pyrrolo[3,4-c]pyridin-3-one;

1-(2-dodecyloxyphenyl)-1-hydroxy-1,2-dihydro-3H-pyrrolo[3,4-c]pyridin-3-one;

1-(3-octodecyloxyphenyl)-1-hydroxy-1,2-dihydro-3H-pyrrolo[3,4-c]pyridin-3-one;

1-[3-(dodecylthio)phenyl]-1-hydroxy-1,2-dihydro-3H-pyrrolo[3,4-c]pyridin-3-one;

1-(3-dodecyloxyphenyl)-1-methoxy-1,2-dihydro-3H-pyrrolo[3,4-c]pyridin-3-one;

1-hydroxy-1-(3-(propen-3-yl)oxyphenyl)-1,2-dihydropyrrolo[3,4-c]pyridin-3-one;

1-hydroxy-1-(3-hydroxyphenyl)-1,2-dihydropyrrolo[3,4-c]pyridin-3-one;

1-hydroxy-1-(3-octylphenyl)-1,2-dihydropyrrolo[3,4-c]pyridin-3-one;

1-hydroxy-1-(3-(4-nonylphenyl)phenyl)-1,2-dihydropyrrolo[3,4-c]pyridin-3-one;

1-[3-(dodecyloxy)phenyl]-5-(2-ethoxy-2-oxoethyl)-1-hydroxy-3-oxo-2,3-dihydro-1H-pyrrolo[3,4-c] pyridin-5-ium bromide;

1-[(3-(dodecyloxy)phenyl)-1-hydroxy-5-[2-(3-hydroxypropoxy)-2-oxyethyl]-3-oxo-2,3 dihydro-1H-pyrrolo[3,4-c]pyridin-5-ium bromide;

ethyl 3-aminocarbonyl-[4-(3-dodecyloxybenzoyl)-1,4-dihydropyridin-1-yl]acetate;

3-hydroxypropyl 3-aminocarbonyl-[4-(3-dodecyloxybenzoyl)-1,4-dihydropyridin-1-yl]acetate;

in the form of a base or an acid addition salt, as well as in the form of a pharmaceutically acceptable hydrate or solvate.

9. Method for the preparation of a compound of general formula (I according to claim 1 in which R1 and R2 together form a single bond and R3 represents —OH, comprising the step of coupling a compound of general formula (II):

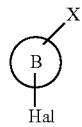

(II)

and a compound of general formula (III):

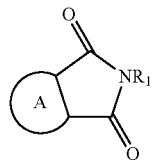

(III)

resulting in a compound of formula (IV) :

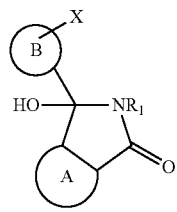

(IV)

in which

and R1 are defined as in general formula (I), Hal represents a halogen atom and X represents a hydrogen atom, when

is not substituted, or the substituent of

corresponding to the desired general formula (I) (in these two cases, the compound (IV) corresponds to the compound (I)), or a halogen atom, the coupling being followed in this case by the reaction substituting the halogen atom of the compound (IV) with the appropriate substituent of

corresponding to the desired general formula (I).

10. Method for the preparation of a compound of general formula (I) according to claim 1 in which R1 and R2 together form a single bond and R3 represents —OH, comprising the step of cyclising compounds of general formula (V):

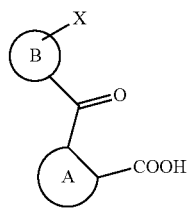

(V)

in which

and Hal are defined as in general formula (IV) in the presence of NHR1 (V'), resulting in the compound of formula (IV):

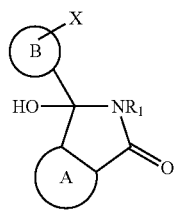

(IV)

in which R1 is defined as in general formula (I) and X represents a hydrogen atom, when

is not substituted, or the substituent of

corresponding to the desired general formula (I)(in these two cases, the compound (IV) corresponds to the compound (I)), or a halogen atom, the cyclisation being followed in this case by the reaction substituting the halogen atom of the compound (IV) with the appropriate substituent of

corresponding to the desired general formula (I).

11. Method according to claim 9 for the preparation of a compound of general formula (I) in which

represents a pyridinium ring in which the nitrogen atom is quaternised, the preparation method further comprising the subsequent step of quaternising the compound of general formula (I) in which

represents a pyridine ring using a compound of general formula (XII):

R-Hal      (XII)

in which Hal represents a halogen atom and R represents a group of the —CH$_2$E type, E being an electron-attracting group as defined in claim 1.

12. Method for the preparation of a compound of general formula (I) in which

represents a dihydropyridine ring and R2 and R3 together form an =O group and R1 represents a hydrogen atom, said method comprising the method according to claim 11 followed by the step of reducing the compound of general formula (I) in which

represents a pyridinium ring.

13. Method according to claim 9, further comprising the reaction to isolate and/or purify the obtained product.

14. Pharmaceutical composition comprising as an active ingredient a compound of general formula (I):

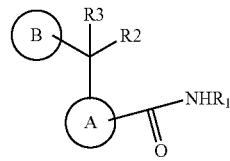

in which:
the cycle

represents a 6-membered aromatic optionally comprising one or more nitrogen atoms, said nitrogen atom(s) optionally being substituted by an optionally substituted tetrahydrofuran group, such as 2-hydroxymethyl-tetrahydrofuran-3,4-diol; or by a —CH$_2$-E group, wherein E represents an electron-attracting group such as —CONRR'; —CO—SR; —CO—Oalkyl; —CO—Oalkyl-OH; —O-alkyl-OAc; phenyl substituted for example by a CN or NO$_2$ group; wherein R and R' are the same or different and independently represent a hydrogen atom or an alkyl group;

and/or wherein said nitrogen atom(s) may be in the form of pyridinium salts, the counter ion being the anion of a halogen atom, such as bromide;

represents a 5-to-10-membered mono- or bicyclic aryl group or heteroaryl group comprising one to three N atoms, substituted by one or more groups selected from the groups —OH; —(C$_5$-C$_{20}$)alkyl; —O(C$_2$-C$_{20}$)alkyl; —S(O)$_p$alkyl wherein p=0, 1 or 2 ; alkenyl; alkynyl; -Oalkenyl; —C(=)O-alkyl; —C(=O)-alkenyl; phenyl optionally substituted by an alkyl group; cycloalkyl optionally substituted by an alkyl group;

R1 represents a hydrogen atom or an alkyl group and R2 and R3 together form an =O group;

or alternatively R3 represents an —OH or —Oalkyl group and R2 forms, together with R1, a single bond;

the groups —C(=O)NHR1 and C(R3)(R2)— being understood to be located in two adjacent positions on the ring

in the form of a base or an acid addition salt, as well as in the form of a pharmaceutically acceptable hydrate or solvate;

and at least one pharmaceutically acceptable excipient.

15. A method for the treatment of tuberculosis comprising administering the compound according to claim 1.

* * * * *